Figure 1A:
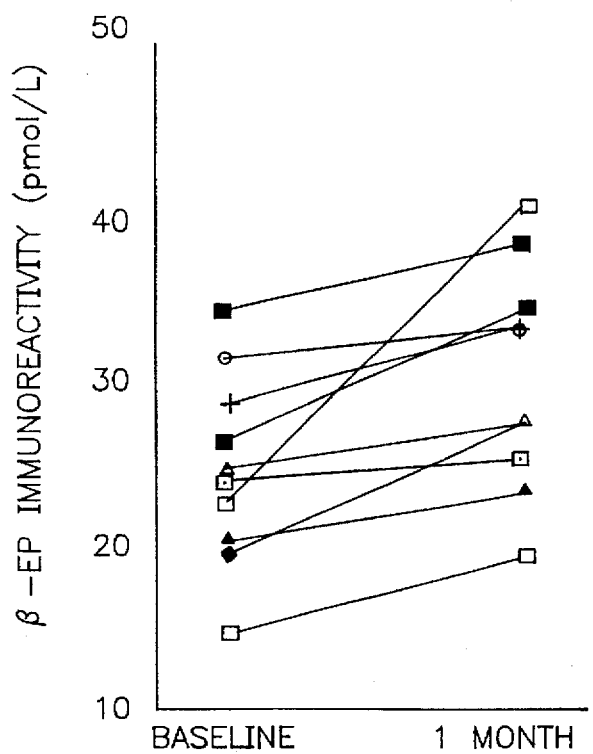

US005736515A

United States Patent [19]

Bengtsson et al.

[11] Patent Number: 5,736,515
[45] Date of Patent: Apr. 7, 1998

[54] USE OF GROWTH HORMONE FOR INCREASEMENT OF CONCENTRATION OF GH, IGF-I AND IGFBP-3 IN CEREBROSPINAL FLUID

[75] Inventors: Bengt-Åke Bengtsson; Olle G. P. Isaksson; Jan-Ove Johansson, all of Göteborg, Sweden

[73] Assignee: Pharmacia & Upjohn Aktiebolag, Stockholm, Sweden

[21] Appl. No.: 602,728

[22] PCT Filed: Sep. 21, 1994

[86] PCT No.: PCT/SE94/00875

§ 371 Date: May 17, 1996

§ 102(e) Date: May 17, 1996

[87] PCT Pub. No.: WO95/08345

PCT Pub. Date: Mar. 30, 1995

[30] Foreign Application Priority Data

Sep. 21, 1993 [SE] Sweden ................................. 9303068

[51] Int. Cl.[6] .......................... A61K 38/00; A61K 38/27
[52] U.S. Cl. .................... 514/12; 514/21; 424/422; 424/424
[58] Field of Search .................. 514/12, 21; 424/422, 424/424

[56] References Cited

U.S. PATENT DOCUMENTS

| 2,974,088 | 7/1961 | Lewis et al. | 167/74 |
|---|---|---|---|
| 3,118,815 | 1/1964 | Li | 167/74 |
| 4,521,409 | 6/1985 | Bauman | 514/21 |
| 4,670,249 | 6/1987 | Ivy et al. | 424/424 |
| 4,693,973 | 9/1987 | Buell | 435/68 |
| 4,786,501 | 11/1988 | Janski et al. | 424/422 |
| 4,857,506 | 8/1989 | Usami et al. | 503/200 |
| 4,977,140 | 12/1990 | Ferguson et al. | 514/12 |

FOREIGN PATENT DOCUMENTS

| 0 103 395 | 8/1984 | European Pat. Off. . |
|---|---|---|
| 0 146 703 | 7/1985 | European Pat. Off. . |
| 0 210 039 | 1/1987 | European Pat. Off. . |
| 0 210 219 | 2/1987 | European Pat. Off. . |
| 0 211 691 | 2/1987 | European Pat. Off. . |
| 0 216 485 | 4/1987 | European Pat. Off. . |
| 0 278 103 | 8/1988 | European Pat. Off. . |
| 0 283 458 | 3/1989 | European Pat. Off. . |
| 223 842 | 7/1990 | New Zealand . |

OTHER PUBLICATIONS

McGauley, Quality of Life Assessment Before and After Growth Hormone Treatment in Adults with Growth Hormone Deficiency, Acta Paediatr Scand Suppl, 1989, 356, 70–72.

McGauley, Psychological Well–Being Before and After Growth Hormone Treatment in Adults with Growth Hormone Deficiency, Horm Res (Switzerland), 1990, 33 Suppl. 4, 52–54.

Cohick and Clemmons, Ann. Review Physiol (55): 131–53 (1993).

McGauley et al., Acta Paediatr. Scand. Suppl. 33 (4), 52–54 (1990).

Primary Examiner—Robert J. Hill, Jr.
Assistant Examiner—P. Lynn Touzeau
Attorney, Agent, or Firm—Pollock, Vande Sande & Priddy

[57] ABSTRACT

A method for treatment of a patient for obtaining an increased concentration of a factor selected from the group consisting of growth hormone, insulin-like growth factor (IGF-I) and IGFBP-3 in cerebrospinal fluid by administration of growth hormone or analogues thereof to a patient in need of said treatment.

8 Claims, 4 Drawing Sheets

USE OF GROWTH HORMONE FOR INCREASEMENT OF CONCENTRATION OF GH, IGF-I AND IGFBP-3 IN CEREBROSPINAL FLUID

The invention relates to the use of growth hormone (GH) or analogues thereof for the production of a medicament giving an increased concentration of GH, Insuline-like growth factor I (IGF-I), IGFBP-3 and β-endorphin immunoreactivity in cerebrospinal fluid.

Introduction

Adult patients with unsubstituted growth hormone deficiency often complain of general fatigue, lack of concentration and memory disabilities. The fatigue reduces their overall working capacity with negative consequences for the patients' career and daily activities. During recent years methods to assess quality of life in a validated way have disclosed the quality and magnitude of psychosocial problem associated with growth hormone deficiency in adults (1).

Treatment of patients with growth hormone deficiency with recombinant human growth hormone (rhGH) has recently been shown to affect the patients psychological well-being (1,2) within only a few weeks. The physiological mechanisms behind this improvement are not known, but could be due to a direct effect of GH on cells in the brain or be secondary to the production of low molecular weight substances that pass the blood-brain-barrier. The effect could also be the result of an alteration in body composition that occurs as a result of GH treatment. Interestingly, GH receptors have been found on many locations in the brain, e.g. the choroid plexus, the hippocampus, the hypothalamus and the pituitary gland (3,4). The presence of GH receptors in the choroid plexus has been suggested to be involved in a mechanism for transport of the hormone over the blood-brain barrier (4). GH has been found in low concentrations in the cerebrospinal fluid (CSF) in humans (5) but it is not known if rhGH crosses the blood-CSF barrier. Intraperitoneal injection of $^{125}$I-labeled rat GH results in an accumulation of radioactivity in several brain areas, suggesting that GH crosses the blood-brain barrier in the rat (6). Moreover, insuline-like growth factor I (IGF-I) has been isolated from the human brain (6a) and there is a wide distribution of IGF-I receptors throughout the brain (6b).

β-endorphins, which mainly are produced in the pituitary and hypothalamus, have been associated with mood enhancement after exercise (7). It has also been suggested that depression is associated with hypoactivity of the endogenous opiodergic system, whereas mania reflects hyperactivity of the system (8). Also in affective disorders changes in the monoamine concentrations have been found (9), and GH treatment of normal and hypophysectomized rats influences the cerebral concentrations of monoamines (10).

To characterize the biochemical changes of patients with growth hormone deficiency in response to rhGH we have studied the effects of one month treatment with rhGH on the concentrations of GH. IGF-I, IGFBP-3, opioid peptides, neuropeptides and monoamine metabolites in the cerebrospinal fluid.

The invention relates to the use of growth hormone or analogues thereof for the production of a medicament giving an increased concentration of growth hormone in cerebrospinal fluid.

It also relates to the use of growth hormone or analogues thereof for the production of a medicament giving an increased concentration of IGF-I, IGFBP- and β-endorphin immunoreactivity in cerebrospinal fluid.

The medicament can be used as an antidepressant.

It has been noticed that the growth hormone given passes the blood-cerebrospinal fluid barrier and thus gives an increased concentration of growth hormone in cerebrospinal fluid.

The treatment preferably lasts at least one month and the amount of GH is preferably 0.1–3 U/kg/week.

The medicament can be for treatment of damages in the brain and for treatment of damages in the memory function of the brain and degenerative disorders of the brain.

Ischemic damages to the brain and dementia are examples of possible medical indications.

The medicament comprises preferably recombinant growth hormone, such as Genotropin®. By analogue is meant a peptide having essentially the same peptide chain as growth hormone and giving the same wanted physiological effect as growth hormone.

Subjects and Methods

Study design

This was a double-blind placebo-controlled study using rhGH (Genotropin®, Kabi Pharmada, Stockholm, Sweden) in 20 patients with established growth hormone deficiency. The patients were studied for a period of one month. The nature of the study was explained to the patients, and their written informed consent was obtained. Kabi Pharmacia provided the randomization codes, which were broken only after the last patient had completed the study. The study protocol was approved by the ethical committee of the medical faculty of the University of Göteborg and the Swedish Board of Health, Stockholm.

Treatment

The dosage of rhGH was 0.25 U/kg/week, administered s c by the patient before bedtime. The maximum daily dose was 4 U. The placebo vials contained the same vehicle as the rhGH vials and were indistinguishable from them. The vials of rhGH contained 16 U (5.92 mg). Between the injections, opened vials were stored in a refrigerator (Temperature between 5°–12° C.) and protected from light for a maximum of 7 days.

Study protocol

Patients were studied as consecutive in-patients in the endocrine ward for one day before treatment with placebo or active therapy, and thereafter at 1 month after start of treatment with placebo or rhGH. The patients fasted and were confined to bed from midnight before the lumbar puncture that was performed at 8.00 to 9.00 the following day. Only hormone-replacement medication was taken in the morning. With the patient in a lateral recumbent position the $L_3$–$L_4$ or $L_4$–$L_5$ interspace was punctured using a 22 gauge needle. The first 12 mL of CSF collected were thoroughly mixed. From this portion 1 mL aliquots were frozen after centrifugation. The remaining CSF was used for cell count, cytology, quantitation of albumin and IgG and isoelectric focusing. The 13th and 14th mL of CSF collected were frozen immediately at bedside for later analysis of gamma-aminobutyric acid (GABA). The 15th to 25th mL of CSF were collected in 2 mL portions mixed with protease-inhibitors and frozen at bedside for later analysis of endorphins, neuropeptides, hGH and IGF-I. Serum was collected simultaneously with CSF and frozen in aliquots. All samples were kept at −80° C. until analyzed.

Patients

Twenty patients, 30–65 years, who previously had been investigated as in-patients at the Division of Endocrinology because of adult-onset pituitary insufficiency after insulin induced hypoglycaemia, all patients had serum GH concentration below 5 mU/L were asked to participate in the study.

All patients had been treated with adequate replacement therapy of glucocorticoids (cortisone acetate 25–50 mg/day), thyroid hormones (L-T4, 0.1–0.15 mg/day), and sex hormones. None of the patients had previously been treated with GH. The characteristics of the 20 patients in the study groups are shown in Table 1.

Analytical methods

CSF cells were counted in a Fuchs-Rosenthal chamber. Cytological preparations were carried out in a cytocentrifuge and stained with May-Grünwald-Giemsa solution.

Albumin and IgG were measured in CSF and serum using nephelometric technique including kit standards (Behring Nephelometer Analyser). The imprecision was <5% (total CV) at 43.6 g/L and 234 mg/L for albumin and 13.7 g/L and 34.7 mg/L for IgG. Albumin ratio (CSF albumin/serum albumin x 1000) was used to evaluate the blood-CSF barrier. IgG-index was calculated as a quantitative measure of local IgG synthesis (11). Isoelectric focusing was performed in polyacrylamide gels stained with silver stain (12). Intrathecal IgG-production was verified by immunoblot technique using antism against the gamma chain of human IgG. Local IgG synthesis was defined as two or more CSF enriched IgG bands.

Beta-2-microglobulin was determined in CSF and serum using ELISA (13) (A 972 and P 174 Dakopatts a/s, Copenhagen, Denmark). Total coefficient of variation was <5% at 2.07 mg/L and 1.04 mg/L for serum and CSF, respectively.

Opioid peptides

CSF samples were collected directly into prechilled polypropylene tubes (Cryotubes, Nunc, Denmark) containing phosphate buffer with 0.1% bovine serum albumin, 0.34 M $K_3$-EDTA and peptidase inhibitors (final concentrations 20 μmol/L bestatin, 0.1 μmol/L thiorphan, 1 μmol/L captopril, 1000 Kallikrein IU/mL and 2 μmol/L PMSF).

Enkephalin RIA assays were carried out using an anti-[$Leu^5$] and [$Met^5$]-enkephalin rabbit antibody (RA-08-099, Cambridge Research Biochemicals, Diagnostika, Falkenberg, Sweden) with 100% cross-reactivity with Leu-enkephalin, 50% cross-reactivity with Met-enkephalin, 2% cross-reactivity with β-endorphine and <1% cross-reactivity with Met-enkephalin sulphoxide, Dynorphin A, Vasoactive Intestinal Peptide (VIP), Neuropeptide Y (NPY), Corticotropin Releasing Factor (CRF) or Somatostatin 14 (SS 14). Leu-enkephalin standard (No 8601) was from Peninsula Laboratories, Inc, (Merseyside, UK) and [$^{125}$I]-Leu-enkephalin (Du Pont, NEN division, Germany) was used as tracer. The lowest level of quantitation was set to 1.0 pmol/L for enkephalin immunoreactivity.

Dynorphin ARIA assays were carried out using an anti-Dynorphin A (1-17) rabbit antibody (RAS 8730), unlabeled Dynorphin A (No 8730) and [$^{125}$I]-Dynorphin A from Peninsula Laboratories, Inc. This antibody reacts for 100% with Dynorphin A 1-17, 42% Dynorphin A 1-13, 30% with Dynorphin A 1-10 $NH_2$, 4% with Dynorphin 1-10, 0.02% with Dynorphin A 1-9 and has <1% cross-reactivity with Met-, Leu-enkephalin, β-endorphin, VIP, NPY, CRF or SS 14. The lowest level of quantitation was set to 7.8 pmol/L.

For β-endorphin RIA assays the anti-β-endorphin rabbit antibody N 1621 (Amersham, Aylesbury, UK) was used. This antibody has 1–2% cross-reactivity with β-lipotropin and <1% cross-reactivity with β-endorphin, Met-, Leu-enkephalin, VIP, NPY, CRF or SS 14. The non-radioactive standard (No 8616) was purchased from Peninsula Laboratories, Inc. and the 3-[$^{125}$I]iodotyrosyl-β-endorphin was from Amersham. The lowest level of quantitation was set to 4.0 pmol/L.

RIA assay for VIP was performed using antibody RA-08-115 and non radioactive standard PP-05-2283 A (Cambridge Research Biochemicals) and radioactive tracer IM.158 from Amersham. The antibody specificity was 100% for native VIP, 70% for VIP 1–28 and <1% cross-reactivity with Met-, Leu-enkephalin, β-endorphin, NPY, CRF or SS 14. The lowest level of quantitation was set to 2.0 pmol/L.

RIA assay for Somatostatin 14 was performed with antibody RAS 8001 (Peninsula Laboratories, Inc), non radioactive standard PP-05-2254A (Cambridge Research Biochemicals) and native iodinated tracer IM.161 from Amersham. The antibody specificity was 100% Somatostatin 14, 100% Somatostatin 28, 100% Somatostatin 25, and according to our own tests 69% Met-enkephalin, 16% Leu-enkephalin, 14% Dynorphin A, 8% β-endorphin, 16% VIP, 20% CRF and <1% for NPY. The lowest level of quantitation was set to 8.2 pmol/L.

For the RIA assay of CRF antibody RA-08-082 and non radioactive standard PP-05-1004 (Cambridge Reasearch Biochemicals), iodinated tracer IM.189 Amersham were used. The antibody reactivity was 100% human CRF and <1% cross-reactivity with Met-, Leu-enkephalin, β-endorphin, V/P, NPY or SS 14. The CSF-samples were first run through a HPLC fractionation step (14) and the lowest level of quantitation was set to 8.2 pmol/L.

All standards and samples were kept in polypropylene tubes and all incubations with antisera were done at 4° C. over night (or longer) using a 0.1 M sodium phosphate buffer with 50 mM sodium chloride and pH 7.4, containing 0.1% bovine serum albumin (Sigma, St Louis, USA), 0.1% sodium azide and 0.1% (v/v) Triton X-100. A polydonal sheep anti-rabbit antibody (Decanting suspension No 3, Pharmacia, Sweden) was used for precipitation at room temperature. All samples were run as duplicates.

The within series coefficient of variation of the RIA assays was calculated from a CSF-control spiked with the respective peptides and found to be for the Met- and Leu-Enkephalin assay 9% (at 5 pmol/L, n=4), Dynorphin A assay 3.4% (at 50 pmol/L, n=4), β-endorphin assay 4.9% (at 40 pmol/L, n=4), VIP assay 10.6% (at 50 pmol/L, n=10), Somatostatin 14 assay 2.5% (at 110 pmol/L, n=4) and CRF 3.3% (at 100 pmol/L, n=4). The total CV of the CRF assay (including HPLC) was 13.8% (at 44 pmol/L, n=18).

Gamma-aminobutyric add

CSF (400 gL) was ultrafiltrated in UFC3LC00 (Ultrafree-MC Low Binding Cellulose, Millipore, Göteborg, Sweden) microcolumns and the amino acids derivatized with FMOC-reagent and separated on reversed phase HPLC (HP 1090, Hewlett Packard Company, Palo Alto, Calif. equipped with a Perkin-Elmer LS-4 fluorimeter (Perkin-Elmer Corp., Norwalk, Conn.) and a HP 1000 chromotography datasystem) essentially according to Einarsson et al (15). The column was a HICHROM S5 C8 (Hichrom Limited, Theale, UK) 200×4.5 mm column. The gradient was made up of a 20 mM Citric add buffer, a 20 mM Sodiumcitrate buffer and Tetrahydrofuran and run for 35 min with increasing pH and decreasing polarity at 1.0 mL/min. The lowest level of detection was set at 30 nmol/L with a recovery of 100%, and the within series coefficient of variation calculated from a CSF-control was 3% (at 340 nmol/L, n=15).

Determination of 3-metoxy-4-hydroxyphenylethyleneglycol (MHPG); 5-hydroxyindoleacetic acid, (5-HIAA); 4-hydroxy-3-metoxyphenylacetic acid (homovanillic acid, HVA) in CSF.

CSF samples were thawed and diluted 1:1 (v/v) in 50 mM sodium acetate buffer pH 4.00, containing 250 mg/L $Na_2$-EDTA, 250 mg/L reduced glutathione and 500 nmol/L 4-hydroxy-3-metoxyphenyllactic acid (MHPLA) as internal standard. 80 µL aliquots were injected into an HPLC system (Kontron Instruments, Zurich, Schwitzerland) and run in a single series. The separation was carried out in a reverse phase mode on an Ultrasphere ODS column, 5 µm particle size, 250 mm×4.6 mm I.D., (Beckman Instruments, San Ramon, Calif., USA) essentially according to Ojala-Karlsson et al. (16). The mobile phase consisted of a mixture of 50 mM acetic add, 45 mM citric acid, 0.3 mM $Na_2$-EDTA and 3.5% (v/v) methanol at pH 5.20±0.02. An electrochemical detector Coulochem II (ESA Inc., Badford, Mass., USA) with conditioning cell (Model 5021) and high sensitivity analytical cell (Model 5011) was used. The electrode potentials were optimized for best sensitivity and selectivity and a calculated ratio of the signal from cells 1 and 2 conferred selectivity to the analytical system. The signal from analytical cell 2 was used for quantification using a multipoint calibration curve with the internal standard method. The within series coefficient of variation was 4.2%, 8.9% and 4.2% for MHPG (25.5 nM), 5-HIAA (318.4 nM) and HVA (153.7 nM) respectively. (A Grzegorczyk et al unpublished).

Insulin-like growth factor 1 (IGF-I) levels in plasma were determined with a RIA kit from Nichols Institute, Wijehen, The Netherlands. The soluble IGF-I was separated from the binding protein using an add-ethanol and alkaline precipitation step.

The IGF-I levels in CSF were measured after a C 18 Sep-Pak column extraction according to the RIA kit.

Insulin-like growth factor binding protein-3 (IGFBP-3) levels in plasma was determined with a KIA kit from Nichols Institute, Wijehen, The Netherlands. hGH levels in serum was determined with a radioimmunometric assay from Pharmacia, Uppsala, Sweden. The hGH standard in the kit was calibrated against the first international standard 80/505 from WHO. Growth hormone levels in 1 mL of urine, 500 µL and 250 µL of CSF (15–25th mL) was measured with an immunometric assay for urinary growth hormone (BioMerieux, France). The method had a detection limit of 1.3 µU/L of GH and the total coefficient of variation for the method was <8% (mean 8.8 µU/L, n=62), 5.6% (mean 45.8 µU/L, n=60) and 7.4% (mean 98.3 µU/L, n=59). The assay was calibrated against the first international standard from WHO (80:505; 2.6 U/mg). The linearity of the method was tested with a serial dilution procedure of both urine and CSF samples. The dilution curves were parallel to the standard curve thus excluding unspecific crossreactivity. All samples were run as duplicates.

Statistical methods

Descriptive values are given as the mean ± standard error of the mean (SEM). The differences between the groups at baseline were analysed with Mann-Whitney, non-parametric test as well as by cluster analysis and principal component analysis (17). The differences between the treatment groups of the values obtained at baseline and after 1 month were analysed separately with the one-sample permutation test. The correlation between two variables was calculated with Spearman's rank correlation test. Two-tailed p-values are quoted.

Results

Differences between the rhGH and placebo groups at baseline.

Since there was a tendency for differences between the two groups for several variables although not statistically significant, duster analysis was performed based on the data for serum GH, CSF GH, urinary GH, plasma IGF-I, plasma IGFBP-3, CSF β-endorphin, CSF 5-HIAA, CSF HVA, age, body mass index and the duration of growth hormone deficiency. No grouping could be shown except between men and women.

In addition, principal component analyses were performed based on all variables for all individuals at baseline. There was no distinct separation between the two groups although, with the limited number of patients included, a tendency towards a skewed distribution was observed.

There were only statistically significant differences (P<0.05) between the two groups at baseline for four of the variables analysed. In the rhGH group 5-HIAA concentration was higher (159.8 vs 99.3 nmol/L, P=0.01), serum-albumin concentration was higher (39.8 vs 36.3 g/L, P=0.01), IgG-index was higher (0.47 and 0.42, P=0.02) and dynorphin A concentration was higher (12.4 and 5.6 pmol/L).

Principal component analyses were also employed to evaluate the effect of treatment and a distinct separation between individuals receiving placebo or receiving rhGH was noted. In the following paragraphs the changes in inidividual variables will be commented on separately.

Eight patients had a blood-brain-barrier damage as indicated by albumin ratio >7.0 at baseline. All patients had normal CSF cell counts and IgG index. Four patients had signs of intrathecal IgG production at isoelectric focusing.

Effects of rhGH treatment

There were statistically-significant differences between the changes in several CSF variables after one month of rhGH treatment between the rhGH and placebo group: The CSF concentrations of GH (p<0.001), IGF-I (p<0.001), IGFBP-3 (p<0.001), HVA (p=0.02) and beta-endorphin immunoreactivity (p<0.001).

Lumbar CSF pressure, serum and CSF albumin and $\beta_2$ microglobulin concentrations, albumin ratio and IgG index During treatment with rhGH lumbar pressure remained unchanged. The mean serum albumin concentration decreased from 39.8±0.7 to 34.8±1.0 g/L (p=0.01) but the CSF albumin concentration remained unchanged. Thus, the albumin ratio increased during rhGH treatment from 6.7±0.8 to 8.0±0.8 (p=0.01) but IgG index remained unchanged. Serum $\beta_2$ microglobulin increased during rhGH treatment from 1.69±0.07 to 1.96±0.1 mg/L (p=0.02) but the CSF $\beta_2$ microglobulin was unchanged (Table 4).

β-endorphin, enkephalin and dynorphin A immunoreactivities

For patients receiving rhGH the mean concentration of β-endorphin immunoreactivities in CSF increased from 24.4±1.8 to 29.9±2.1 pmol/L (p=0.002) (FIG. 1a). During rhGH treatment the enkephalin immunoreactivities remained unchanged (Table 3). For the dynorphin A reactivity no change within the individuals was observed during the study (Data not shown).

MHPG, 5-HIAA and HVA

Figure 2A:
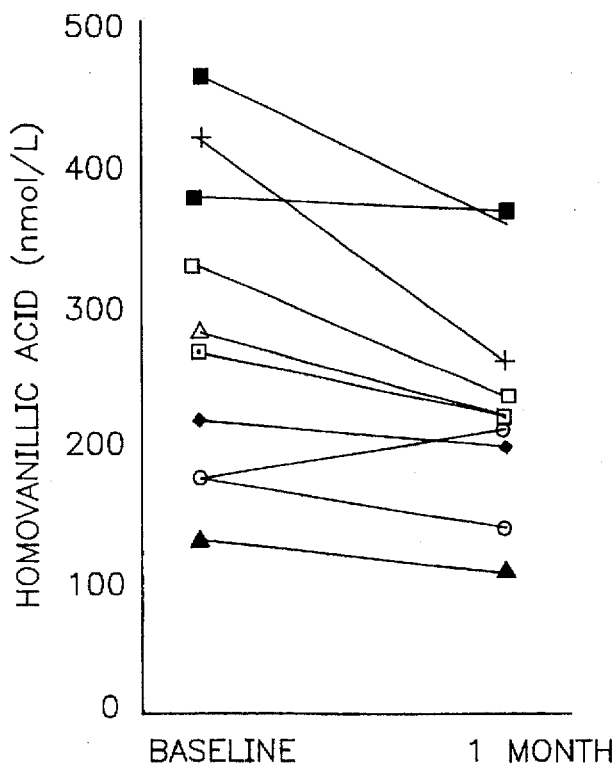

The concentrations of MHPG and 5-HIAA in CSF were unchanged during treatment with rhGH while the concentration of HVA decreased from 282.1±36.0 to 234.3±96.5 nmol/L (p=0.02), Table 3 (FIG. 2a).

VIP, CRF, Somatostatin and GABA

The concentration of VIP in CSF decreased from 4,1±0,6 to 3,7±0,4 pmol/L (p=0,03). The concentrations of CRF and Somatostatin immunoreactivitites in CSF remained unchanged during treatment with rhGH as did the concentration of GABA, Table 3.

Serum and urine GH concentration, plasma IGF-I and IGFBP-3 concentrations, and CSF GH, IGF-I and IGFBP-3 concentrations During rhGH treatment the plasma concentrations of IGF-I increased from 90.4±7.9 to 342.3±41.2 µg/L (p=0.002) and IGFBP-3 from 1.71±0.24 to 2.98±0.22 mg/L (p=0.002). Serum GH concentration rose from 0.05±0.03 to 3.92±0.92 mU/L (p=0.002). During rhGH treatment the CSF concentration of GH increased tenfold from 13.3±4.4 to 149.3±22.2 μU/L (p=0.002) (FIG. 3a) and CSF IGFBP-3 increased from 13.4±1.25 to 17.5±1.83 μg/L (p=0.002) (Table 2). The CSF concentration of IGF-I increased from 0–67±0.04 to 0.99±0.10 μg/L (p=0.005).(FIG. 4 and Table 2).

The relationship between the change of CSF GH concentration and the changes of the concentrations of endogenous opioids, neuropeptides and monoamine metabolites during rhGH treatment There was a positive relationship (Rs:0.57, p<0.05) between the increase in GH concentration in CSF and the increase in β-endorphin immunoreactivity. There was a negative relationship (Rs:0.53, p<0.05) between the increase in GH concentration in CSF and the decrease in HVA. There was no correlation between the change in CSF GH concentration and the changes in immunoreactive enkephalin, dynorphin A, VIP, somatostatin or MHPG, 5-HIAA and GABA concentrations.

The relationship between the change of CSF GH concentration and the changes in CSF IGF-I concentrations during rhGH treatment.

There was no correlation between the increase in CSF GH concentration and the increase in CSF IGF-I concentration. The relationship between the change of CSF IGF-I concentration and the changes in CSF IGFBP-3 and plasma concentrations.

The increase in CFS IGF-I concentration showed a strong positive correlation with the increase in CFS IGFBP-3 (r=0.81, p<0.05). There was no correlation between the increase in CSF IGF-I concentration and the increase in plasma IGF-I.

The relationship between the change of CSF GH concentration and the changes in CSF and plasma IGFBP-3 concentrations and plasma IGF-I concentration The increase in CSF GH concentration correlated with the increase in CSF IGFBP-3 (Rs:0.66, p<0.01), serum IGFBP-3 (Rs:0.67, p<0.01) and serum IGF-I (Rs:0.7, p<0.01).

TABLE 1

Characteristics of the 20 patients in the study groups.

| Characteristic | rhGH | Placebo |
|---|---|---|
| Mean age (yr) | 49.1 | 52.0 |
| Range | 30–64 | 40–65 |
| Sex (M/F) | 5/5 | 5/5 |
| Known duration of hypopituitarism (yr) | 9.4 | 14.2 |
| Range | 2–21 | 2–34 |
| Original diagnosis | | |
| Prolactinoma, chromophobe adenoma, craniopharyngioma | 10 | 7 |
| Pituitary cyst | 0 | 1 |
| Sheehan's syndrome | | 1 |
| Idiopathic hypopituitarism | | 1 |
| Replacement treatment | | |
| Corticosteroid | 5 | 7 |
| Thyroxine | 8 | 8 |
| Gonadal steroids | 5 | 3 |
| Desmopressin | 1 | 3 |
| Height (cm) | 172 ± 3.1 | 173.7± 4.3 |
| Weight (kg) | 79.6 ± 5.7 | 81.4 ± 4.4 |

TABLE 2

Measurements of GH concentration in serum(s) and the cerebrospinal fluid (CSF), urinary GH, insulin-like growth factor I (IGF-I) in plasma, IGF binding protein-3 (IGFBP-3) in plasma and in CSF in patients with Growth Hormone Deficiency treated with rhGH or placebo for 1 month.

| Substance and group | Baseline mean ± SEM | 1 Mo mean ± SEM | P-value |
|---|---|---|---|
| S-GH (mU/L) | | | |
| rhGH | 0.05 ± 0.03 | 3.92 ± 0.92 | 0.002 |
| Placebo | 0.26 ± 0.15 | 0.47 ± 0.35 | |
| CSF-GH (μU/L) | | | |
| rhGH | 13.3 ± 4.4 | 149.3 ± 22.2 | 0.002 |
| Placebo | 9.2 ± 4.9 | 8.3 ± 4.2 | |
| Urinary GH μU/24 h | | | |
| rhGH | 2.9 ± 1.0 | 41.0 ± 7.2 | 0.002 |
| Placebo | 4.6 ± 2.1 | 4.4 ± 2.2 | |
| Plasma-IGF-I conc. (μg/L) | | | |
| rhGH | 90.4 ± 17.9 | 342.3 ± 41.2 | 0.002 |
| Placebo | 88.9 ± 19.1 | 88.8 ± 19.3 | |
| CFS ICF-I conc. (μg/L) | | | |
| rhGH | 0.67 ± 0.04 | 0.99 ± 0.10 | 0.005 |
| Placebo | 0.74 ± 0.05 | 0.72 ± 0.06 | |
| Plasma-IGFBP-3 conc. (mg/L) | | | |
| rhGH | 1.71 ± 0.24 | 2.98 ± 0.22 | 0.002 |
| Placebo | 1.63 ± 0.26 | 1.64 ± 0.25 | |
| CSF-IGFBP-3 conc. (μg/L) | | | |
| rhGH | 13.4 ± 1.25 | 17.5 ± 1.83 | 0.002 |
| Placebo | 12.1 ± 1.24 | 11.8 ± 1.19 | |

TABLE 3

Measurements of endogenous opioids, neuropeptides and monoamine metabolites in the CSF in patients with Growth Hormone Deficiency treated with rhGH or Placebo for 1 month.

| Substance and group | Baseline mean ± SEM | 1 Mo mean ± SEM | P-value |
|---|---|---|---|
| β-endorphin (pmol/L) | | | |
| rhGH | 24.4 ± 1.8 | 29.9 ± 2.1 | 0.002 |
| Placebo | 30.4 ± 2.8 | 29.7 ± 2.5 | |
| Enkephalin (pmol/L) | | | |
| rhGH | 6.6 ± 0.5 | 7.0 ± 0.5 | NS |
| Placebo | 6.8 ± 0.4 | 7.7 ± 1.1 | |
| VIP (pmol/L) | | | |
| rhGH | 4.1 ± 0.6 | 3.7 ± 0.4 | 0,03 |
| Placebo | 3.3 ± 0.4 | 3.3 ± 0.3 | |
| MHPG (nmol/L) | | | |
| rhGH | 38.3 ± 3.2 | 35.8 ± 3.2 | NS |
| Placebo | 32.1 ± 2.1 | 28.2 ± 2.2 | |
| 5-HIAA (nmol/L) | | | |
| rhGH | 159.8 ± 19.3 | 141.0 ± 17.1 | NS |
| Placebo | 99.3 ± 14.0 | 95.5 ± 12.5 | |
| HVA (nmol/L) | | | |
| rhGH | 282.1 ± 36.0 | 234.3 ± 26.5 | 0.02 |
| Placebo | 175.8 ± 37.1 | 180.7 ± 38.6 | |
| GABA (nmol/L) | | | |
| rhGH | 244.1 ± 34.1 | 240.0 ± 26.7 | NS |
| Placebo | 160.5 ± 34.9 | 153.9 ± 31.5 | |

TABLE 4

Measurements of lumbar pressure, serum and CSF albumin concentrations, albumin ratio, IgG index and serum and CSF $\beta_2$-microglobulin concentrations in patients with Growth Hormone Deficiency treated with rhGH or placebo for 1 month.

| Measurement and group | Baseline mean ± SEM | 1 Mo mean ± SEM | P-value |
|---|---|---|---|
| Lumbar CSF pressure (cm H$_2$O) | | | |
| rhGH | 15.1 ± 1.4 | 15.4 ± 1.5 | NS |
| Placebo | 16.6 ± 1.5 | 16.8 ± 1.2 | |
| S-Albumin conc. (g/L) | | | |
| rhGH | 39.8 ± 0.7 | 34.8 ± 1.0 | 0.01 |
| Placebo | 36.3 ± 0.9 | 37.3 ± 1.0 | |
| CSF-Albumin conc. (mg/L) | | | |
| rhGH | 263.5 ± 29.9 | 282.9 ± 31.0 | NS |
| Placebo | 218.7 ± 27.3 | 230.3 ± 28.3 | |
| Albumin ratio | | | |
| rhGH | 6.7 ± 0.8 | 8.0 ± 0.8 | 0.01 |
| Placebo | 6.0 ± 0.7 | 6.1 ± 0.7 | |
| IgG-index | | | |
| rhGH | 0.47 ± 0.1 | 0.45 ± 0.01 | NS |
| Placebo | 0.42 ± 0.02 | 0.42 ± 0.01 | |
| S-$\beta_2$microglobulin (mg/L) | | | |
| rhGH | 1.69 ± 0.07 | 1.96 ± 0.10 | 0.02 |
| Placebo | 1.64 ± 0.16 | 1.61 ± 0.16 | |
| CSF-$\beta_2$microglobulin (mg/L) | | | |
| rhGH | 1.30 ± 0.09 | 1.34 ± 0.09 | NS |
| Placebo | 1.20 ± 0.08 | 1.12 ± 0.05 | |

Discussion

This report, although limited in number of patients, systematically describes changes in several biochemical parameters in CSF as a result of treatment of adult growth hormone deficient patients with rhGH. The random selection criteria, initially chosen to enable psychometric evaluation of treatment, produced a somewhat skewed distribution of individuals in the rhGH and placebo groups. However, the differences were not statistically verified for any of the variables responding significantly to rhGH treatment. Thus, we have shown for the first time that treatment with rhGH of adult patients with growth hormone deficiency significantly raises the concentrations of immunoreactive $\beta$-endorphins, decreases the concentration of homovanillic add and increases the concentration of GH tenfold in the CSF. There was also a significant increase in the CSF concentrations of IGF-I and IGFBP-3.

The molecular identity of the CSF $\beta$-endorphin immunoreactivity, not adressed in this study, will be the subject of a separate investigation using HPLC-fractionation as a first step. The antiserum used is specific for the carboxy-terminal of the $\beta$-endorphin peptide and has very low cross-reactivity with intact $\beta$-lipotrophin as well as with the amino-terminal parts of $\beta$-endorphin molecule such as with Met-enkephalin and $\beta$-endorphin. However, the antibody used may still recognize metabolites or partially modified $\beta$-endorphins.

Opioid peptides stimulate GH release in man (18) independantly of GH releasing hormone (19) and mediate clonidine stimulated GH release (20). Intraventricular administration of $\beta$-endorphins have also been shown to promote GH secretion (21). For the first time we have now shown that GH stimulates the release of $\beta$-endorphins. The mechanism is unclear but it may be a direct effect of GH on $\beta$-endorphin producing cells or secondary to production of low molecular weight substances in peripheral tissues that penetrates the blood-brain barrier.

The mechanism behind the increase of CSF $\beta$-endorphin immunoreactivity could also be due to the decreased homovanillic add concentrations following GH-treatment. In rats dopamine inhibits the release of $\beta$-endorphin in the neurointermediate pituitary, hypothalamus and septum and the dopamine antagonist haloperidol increases the plasma concentrations of $\beta$-endorphin immunoreactivity (22). During treatment with chlorpromazine there was a significant increase in the level of the total opiate activity in the rat brain (23), assumingly reflecting an increased biosynthesis of the peptide.

$\beta$-endorphin immunoreactivity in serum became undetectable after hypophysectomy of patients with metastatic cancer but, although decreased, remained detectable in significant amounts in the CSF (24). This suggests that a considerable amount of $\beta$-endorphin in CSF is of non-pituitary origin. The decline of $\beta$-endorphin concentration in CSF in that study might very well be related to GH deficiency caused by hypophysectomy (24).

The observed increase of $\beta$-endorphin immunoreactivity could possibly explain the improvement of mood usually seen after rhGH treatment. The patient who subjectively improved most had the highest increase of $\beta$-endorphin immunoreactivity. Several studies have shown that an activation of opiate receptors exerts an antidepressant effect (25). Electroconvulsive therapy causes a short-term increase in plasma of $\beta$-endorphin immunoreactivity and may contributing to the positive effects of this treatment in endogenous depression (26).

Simultaneously, to the increase in $\beta$-endorphin immunoreactivity there was a fall in homovanilliic add concentration. It has been shown that GH produces a rapid reduction of dopamine and noradrenaline in the median eminence in rats (27). Changes in brain biogenic amines have been observed as early as 15 min. after an injection with GH. The changes are region dependent and mostly there is a decrease of the brain biogenic amine levels (10).

VIP acts as a neurotransmitter and is present in human CSF. It has a widespread distribution in the brain including the cortex, hippocampus, amygdala, hypothalamus and the anterior pituitary (28). One of its functions is to act as a prolactin releasing factor. The pituitary VIP-cells are activated by hypothyroidism and suppressed by supraphysiological doses of thyroid hormones. (29). GH increases the conversion of $T_4$ to $T_3$ (2) so the decrease in CSF VIP concentration could possibly be explained by this mechanism.

The finding that eight patients had a blood-CSF barrier damage and that four patients had a discrete intrathecal IgG production is not surprising since the majority of the patients had received surgical treatment of their pituitary tumour and/or irradiation. During treatment with rhGH two patients had an increased albumin ratio but this increase was explained by the fall in serum albumin concentration during rhGH treatment which in turn is explained by the expansion of the extracellular fluid volume caused by the antinatriuretic actions of GH (30). Although GH has potent antinatriuretic actions there was no change in the intracranial pressure during rhGH treatment.

We observed a mean tenfold increase in CSF concentration of GH after one month's treatment with rhGH. This suggests that rhGH passes the blood-CSF barrier. This increase was similar in patients with and without blood-CSF barrier damage. This pronounced increase in CSF GH is in contrast to what have been reported from rhesus monkeys. In that study infusion of large amounts of human GH led to only a small change in CSF GH levels (31). However, in that study the measurements of GH in CSF were performed after a single infusion period, in contrast to the present study where the patients were treated for one month. Secondly, the sensitivity for the urinary growth hormone assay used in the present study was approximately 100 to 1000 fold higher than the radioimmunoassay method used by Belchetz et al (31). The mean increase of GH in CSF in our study is tenfold compared with baseline but the the CSF/serum ratio for GH is still only 5%.

The mechanism behind the increase of GH in CSF remains to be elucidated. More than 80% of CSF proteins are derived from serum by ultrafiltration which depend on molecular size. An alternative explanation is a GH receptor-mediated transport in the choroid plexus as has been suggested by Lai et al 1991 (4).

The levels of IGFBP-3 in CSF may arise from the plasma pool (32) but can also be locally produced (33). The mechanism for the increase of serum $\beta_2$-microglobulin in different diseases is not fully understood but cytokine regulated release from immune cells has been postulated (34). Animal experiments have shown that GH influences the proliferation and differentiation of T-lymphocytes (35). We suggest an effect by GH on the immune system as the most plausible cause of the increase in serum $\beta$-microglobulin observed in this study.

In conclusion, we have found that one month of treatment with rhGH of adult patients with growth hormone deficiency increases the concentration of $\beta$-endorphin immunoreactivities in the CSF and simultaneously decreases the concentrations of homovanillic acid and VIP. These changes could possibly explain the improvement in psychological well-being usually observed in patients with growth hormone deficiency shortly after the initiation of treatment with rhGH. The concentration of GH in the CSF increased tenfold showing that rhGH passes the blood-CSF barrier.

Legends

FIG. 1a. Effects of rhGH on CSF $\beta$-endorphin ($\beta$-EP) immunoreactivity in 10 adult patients with growth hormone deficiency.

Figure 1B:
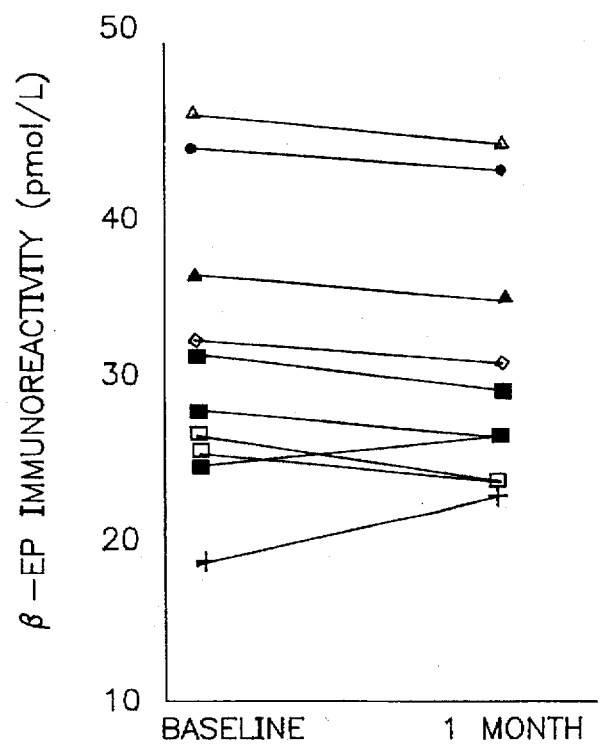

FIG. 1b. Effects of placebo on CSF $\beta$-endorphin ($\beta$-EP) immunoreactivity in 10 adult patients with growth hormone deficiency.

FIG. 2a. Effects of rhGH on CSF homovanillic acid concentration in 10 adult patients with growth hormone deficiency.

Figure 2B:
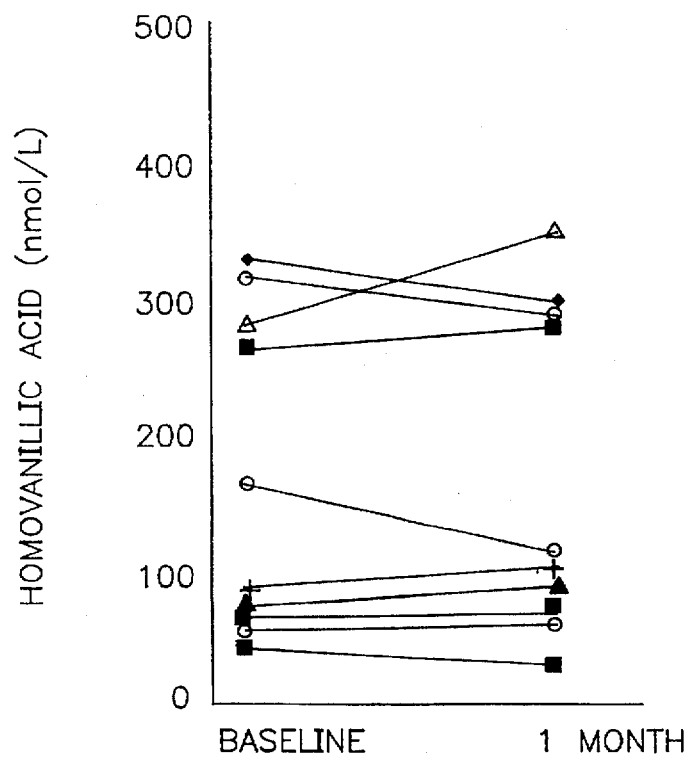

FIG. 2b. Effects of placebo on CSF homovanillic acid concentration in 10 adult patients with growth hormone deficiency.

Figure 3A:
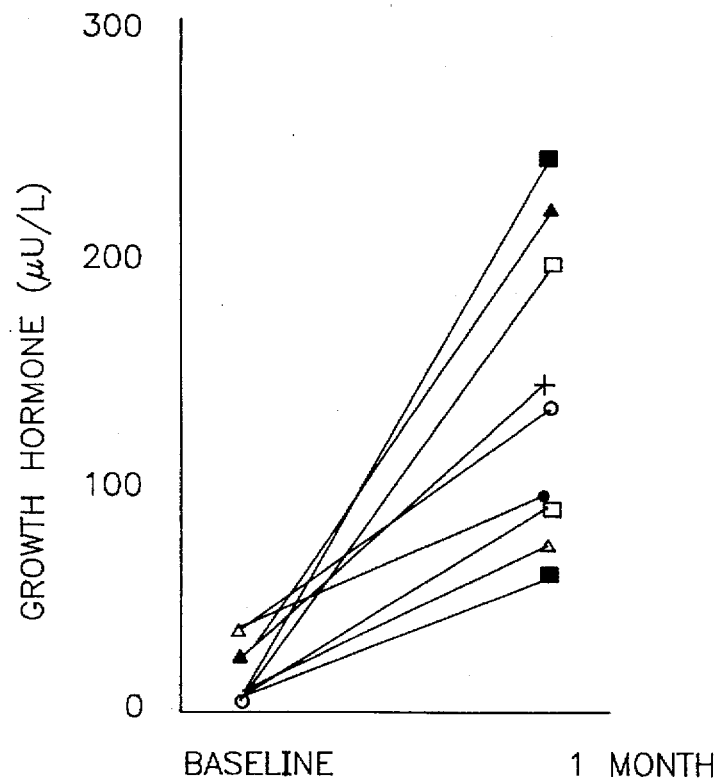

FIG. 3a. Effects of rhGH on CSF GH concentration in 10 adult patients with growth hormone deficiency.

Figure 3B:
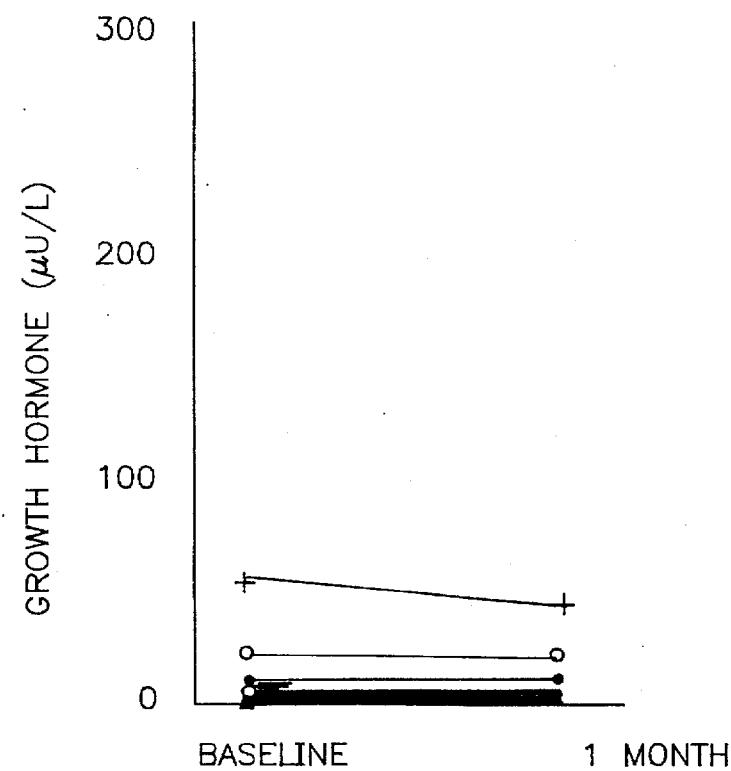

FIG. 3b. Effects of placebo on CSF GH concentration in 10 adult patients with growth hormone deficiency.

Figure 4A:
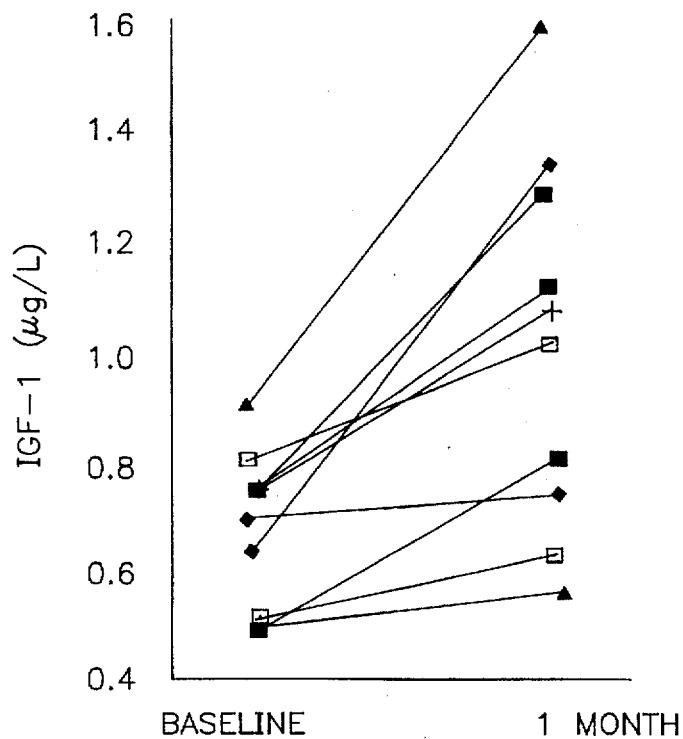

FIG. 4a. Effects of rhGH on CSF IGF-I concentration in 10 adult patients with growth hormone deficiency.

Figure 4B:
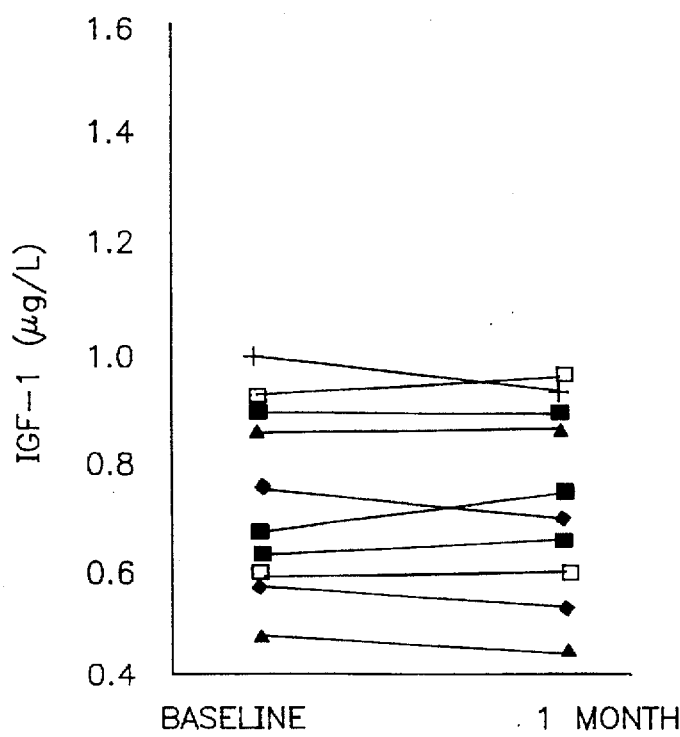

FIG. 4b. Effects of placebo on CSF IGF-I concentration in 10 adult patients with growth hormone deficiency.

In the doubleblind placebo-controlled trial we have thus studied the effects on endogenous opioid peptides, neuropeptides, monoamine metabolites, growth hormone and insulin-like growth factor binding protein-3 (IGFBP-3) in the cerebrospinal fluid during one month of treatment with recombinant human growth hormone in 20 patients with adult onset growth hormone deficiency. All patients received appropriate thyroid, adrenal and gonadal hormone replacement. The dose of recombinant human growth hormone was 0.25 U/kg/week.

In cerebrospinal fluid the mean concentration of immunoreactive $\beta$-endorphin increased from 24.4±1.8 to 29.9±2.1 pmol/L (p=0.002) during recombinant human growth hormone treatment. The dopamine metabolite homovanillic acid decreased from 282.1±36.0 to 234.3±26.5 nmol/L (p=0.02). Vasoactive intestinal peptide decreased from 4.1±0.6 to 3.7±0.4 pmol/L (p=0.03). Cerebrospinal fluid growth hormone concentration increased from 13.3±4.4 to 149.3±22.2 µU/L (p=0.002) and the cerebrospinal fluid IGFBP-3 concentration rose from 13.4±1.25 to 17.5±1.83 µg/L (p=0.002).

There was no significant changes in the cerebrospinal fluid concentrations of enkephalins, dynorphin A, the norepinephrine metabolite 3-metoxy-4-hydroxyphenylethylenglycol, the serotonin metabolite 5-hydroxyindoleacetic acid, gamma-aminobutyric acid, somostatin or corticotropin releasing factor.

We conclude that treatment with recombinant human growth hormone increases the concentration of $\beta$-endorphin immunoreactivities in the cerebrospinal fluid and simultaneously decreases the concentrations of homovanillic acid and vasoactive intestinal peptide. The concentration of growth hormone in the cerebrospinal fluid increased tenfold showing for the first time in humans that recombinant human growth hormone passes the blood-cerebrospinal fluid barrier.

REFERENCES

1. McGauley G A. Quality of life assessment before and after growth hormone treatment in adults with growth hormone deficiency. Acta Paediatr Scand (Suppl) 1989;356:70–72.

2. Bengtsson B-Å, Eden S, Lönn L, Kvist H, Stokland A, Lindstedt G, Bosaeus I, Töllo J, Sjöstroöm L, Isaksson OGP. Treatment of adults with growth hormone (GH) deficiency with recombinant human GH. J Clin Endocrinol Metab 1993;76:309–17.

3. Lobie P E, Lincoln D T, Breipohl W, Waters M J. Growth hormone receptor localization in the central nervous system. Abstract. Proc US Endocr Soc Seattle1989;71:215.

4. Lai Z, Emtner M, Roos P, Nyberg F. Characterization of putative growth hormone receptors in human choroid plexus. Brain Res 1991; 546:222–26.

5. Linfoot J A, Garda J F, Wei W, Fink R, Serin R, Born B L, Lawrence J H. Humans growth hormone levels in cerebrospinal fluid. J Clin Endocrinol Metab 1970; 31:230–32.

6. Stem W C, Miller M, Resnick O, Morgane P J. Distribution of $^{125}$I-labelled rat growth hormone in regional brain areas and peripheral tissue of the rat. Am J Anat 1975;144:503–08.

6a. Carlsson-Skwirut C et al. Isolation and characterization of variant IGF-I as well as IGF-II from adult human brain. FEBS 1986; 201:46–50.

6b. Sara VR et al. Evidence for the presence of specific receptors for insulin-like growth factors I (IGF-I) and II (IGF-II) and insulin throughout the adult human brain. Neurosci Lett 1982;34:39–44.

7. Morgan W P. Affective beneficence of vigorous physical activity. Med Sci Sports Exer 1985; 17:94–100.

8. Byck R. Peptide transmitters: A unifying hypothesis for euphoria, respiration, sleep, and the action of lithium. Lancet 1976;ii:72–73.

9. Baldessarini R J. The basis for amine hypotheses in affective disorders. Arch Gen Psychiatry 1975;32:1087–93.

10. Stern W C, Miller M, Jalowiec J E, Forbes W B, Morgane P J. Effects of growth hormone on brain biogenic amine levels. Pharmacol Biochem Behav 1975b;3:1115–18.

11. Tibbling G, Link H, Öhman S. Principles of albumin and IgG analyses in neurologica disorders. I. Establishment of reference values. Scand J Clin Lab Invest 1977;37:385–90.

12. Wikkelsö C, Andersson M, Andersson R, Blomstrand C. Isoelectric focusing followed by silver staining. A suitable method for routine investigation of cerebrospinal fluid proteins. Eur Neurol 1984;23:306–12.

13. Bjerrum O W, Lage S, Hansen O E. Measurement of beta-2-microglobulin in human cerebrospinal fluid by ELISA technique. Acta Neurol Scand 1986;74:177–80.

14. Venn R F. Combined high-performance liquid chromatographic-radio-immunoassay ethod for the analysis of endorphins, enkephalins and other neurotransmittors. J Chromatogr 1987;423:93–104.

15. Einarsson S, Josefsson B, Lagerkvist S. Determination of amino adds with 9-fluorenylmethylchloroformat and reversed phase high performance liquid chromatograpy. J Chromatogr 1983;282:609–618.

16. Ojala-Karlsson P, Sheinin M. Improved high-performance liquid chromatographic method for the routine determination of unconjugated 3-metoxy-4-hydroxyphenylethyleneglycol in human plasma using solid-phase extraction and electrochemical detection. J Chromatogr 1991;565:131–39.

17. Wold S, Esbensen K, Geladi P. Principal component analysis. Chemometrics and Intelligent Laboratory Systems 1987;2:37–52.

18. Delitala G, Grossman A, Besser M. Differential effects of opiate peptides and alkaloids on anterior pituitary hormone secretion. Neuroendocrinology 1983;37:275–79.

19. Delitala G, Tomasi P A, Palermo M, Ross R J M, Grossman A, Besser G M. Opioids stimulate growth hormone (GH) release in man indepedently of GH-releasing hormone. J Clin Endocrinol Metab 1989;69:356–58.

20. Bruhn T O, Tresco P A, Mueller G P, Jackson IMD. Beta-endorphin mediates doraldine stimulated growth hormone release. Neuroendocrinology 1989;50:460–63.

21. McCann S M. Control of anterior pituitary hormone release by brain peptides. Neuroendocrinology 1980;31:355–63.

22. Holt V, Bergmann M. Effects of acute and chronic haloperidol treatment on the concentrations of immunoreactive β-endorphin in plasma, pituitary and brain of rats. Neuropharmacology 1982;21:147–54.

23. Wise C D, Stein L. Brain endorphin levels increase after long-term chloro-promazine treatment. In: Endorphins in Mental Health (Usdin, E., Bunney Jr W E and Kline N S, Eds.) 1979;115–18. Macmillan Press, London.

24. Schlacter L B, Wardlaw S L, Tindall G T, Frantz A G. Persistence of β-endorphin in human cerebrospinal fluid after hypophysectomy. J Clin Endocrinol Metab 1983;57:221–24.

25. Gerner R H, Catlin D H, Gorelick D A, Hui K K, Li C H. β-endorphin. Intravenous infusion causes behavioural change in psychiatric inpatients. Arch Gert Psychiatry 1980;37:642–47.

26. Alexopoulos G S, Inturrisi C E, Lipman R, Frances R, Haycox J, Dougherty H, Rossier J. Plasma immunoreactive β-endorphin levels in depression. Arch Gen Psychiatry 1983;40:181–83.

27. Andersson K, Fuxe K, Eneroth P, Isaksson O, Nyberg F, Roos P. Rat growth hormone and hypothalamic catecholamine nerve terminal systems. Evidence for rapid and discrete reductions in dopamine and noradrenaline levels and turnover in the median eminence of the hypophysectomized male rat. Eur J Pharmacol 1983;95:271–75.

28. Erason P C, Fahrenkrug J, Spokes EGS. Vasoactive intestinal polypeptide (VIP): distribution in normal human brain and in Huntington's disease. Brain Res 1979;173:174–78.

29. Reichlin S. Neuroendocrine significance of vasoactive intestinal polypeptide. Ann NY Acad Sd 1988;527:431–49.

30. Rosén T, Bosaeus L Tölli J, Lindstedt G, Ben gtsson B-Å. Increased body fat mass and decreased extracellular fluid volume in adults with growth hormone deficiency. Clin Endocrinol 1993;38:63–71.

31. Belchetz P E, Ridley R M, Baker H F. Studies on the accessability of prolactin and growth hormone to brain: effect of opiate agonists on hormone levels in serial, simultaneous plasma and cerebrospinal fluid samples in the rhesus monkey. Brain Res 1982;239:310–14.

32. Gargosky S E, Pham H M, Wilson K F, Liu F, Guidice L C, Rosenfeld R G. Measurement and characterization of insulin-like growth factor binding protein-3 in human biological fluids: discrepancies between radioimmunassay and ligand blotting. Endocrinology 1992;131:3051–60.

33. Hill D J, Han V K M. Paracrinology of growth regulation. J Dev Physiol 1991;15:91–104.

34. Nachbaur K, Troppmair J, Bieling P, Kotlan B, Konig P, Huber Ch. Cytokines in the control of beta-2-microglobulin release. I. In vitro studies on various haemotopoietic cells. Immunobiol 1988;177:55–65.

35. Murphy W J, Durum S K, Longo D L. Role of neuroendocrine hormones in murine T cell development. Growth hormone exerts thymopoietic effects in vivo. J. Immunol 1992;149:3851–57.

We claim:

1. Method for treatment of a patient for obtaining an increased concentration of a factor selected from the group consisting of growth hormone, insulin-like growth factor-I (IGF-I) and IGFBP-3 in cerebrospinal fluid by administration of growth hormone or analogues thereof to a patient in need of said treatment.

2. The method of claim 1 for giving an increased concentration of IGF-I in cerebrospinal fluid.

3. The method of claim 1 for giving an increased concentration of IGFBP-3 in cerebrospinal fluid.

4. The method of claim 1 for giving an increased β-endorphin immunoreactivity.

5. The method of claim 1 for treating a patient in need of an antidepressant.

6. The method of claim 1 which comprises treating for at least one month.

7. The method of claim 1 which comprises administering a medicament containing GH for 0.1–3 U/kg/week.

8. The method of claim 1 wherein said growth hormone or analogues thereof is recombinant growth hormone.

* * * * *